United States Patent
Hall et al.

(10) Patent No.: US 6,751,576 B2
(45) Date of Patent: Jun. 15, 2004

(54) ON-SITE AGRICULTURAL PRODUCT ANALYSIS SYSTEM AND METHOD OF ANALYZING

(75) Inventors: Allen L. Hall, Amelia, OH (US); Alan P. Lundstedt, Cincinnati, OH (US); Ching-Hui Tseng, West Chester, OH (US)

(73) Assignee: Cognis Corporation, Cincinnati, OH (US)

( * ) Notice: Subject to any disclaimer, the term of this patent is extended or adjusted under 35 U.S.C. 154(b) by 79 days.

(21) Appl. No.: 09/802,199

(22) Filed: Mar. 8, 2001

(65) Prior Publication Data

US 2001/0037182 A1 Nov. 1, 2001

Related U.S. Application Data

(60) Provisional application No. 60/188,500, filed on Mar. 10, 2000.

(51) Int. Cl.[7] .................. G06F 11/30; G06F 15/00; G21C 17/00
(52) U.S. Cl. .................. 702/183; 382/100; 356/328
(58) Field of Search .................. 702/183; 382/100; 356/328

(56) References Cited

U.S. PATENT DOCUMENTS

| | | |
|---|---|---|
| 4,146,788 A | 3/1979 | Mirkin et al. |
| 4,247,773 A | 1/1981 | Nexo et al. |
| 4,253,766 A | 3/1981 | Funk |
| 4,260,262 A | 4/1981 | Webster |
| 4,319,491 A | 3/1982 | Christoffersen et al. |
| RE31,023 E * | 9/1982 | Hall, III .................. 47/1 |
| 4,539,649 A | 9/1985 | Michaelis et al. |
| 4,713,781 A | 12/1987 | Brizgis et al. |
| 4,800,279 A | 1/1989 | Hieftje et al. |
| 4,883,963 A | 11/1989 | Kemeny et al. |
| 5,096,294 A | 3/1992 | Layzell et al. |
| RE34,070 E | 9/1992 | Regimand |
| 5,260,875 A * | 11/1993 | Tofte et al. .................. 701/50 |
| 5,308,981 A | 5/1994 | Perten |
| 5,319,437 A | 6/1994 | Van Aken et al. |
| 5,323,322 A | 6/1994 | Mueller et al. |
| 5,327,708 A | 7/1994 | Gerrish |
| 5,357,441 A | 10/1994 | Petty et al. |
| 5,365,462 A | 11/1994 | McBean, Sr. |
| 5,400,138 A | 3/1995 | Peterson et al. |
| 5,406,084 A | 4/1995 | Tobler et al. |
| 5,459,677 A | 10/1995 | Kowalski et al. |
| 5,483,339 A | 1/1996 | Van Aken et al. |
| 5,517,427 A | 5/1996 | Joyce |
| 5,519,219 A | 5/1996 | Alexay et al. |
| 5,537,336 A | 7/1996 | Joyce |

(List continued on next page.)

FOREIGN PATENT DOCUMENTS

| | | |
|---|---|---|
| GB | 2 336 430 A | 2/1998 |
| WO | WO 99/46971 | 9/1999 |

OTHER PUBLICATIONS

M. Otto, *Chemometrics: Statistics and Computer Applications in Analytical Chemistry*, J Am.Chem.Soc., 122 p. 5903–5904 (2000).

*Primary Examiner*—John Barlow
*Assistant Examiner*—Aditya Bhat
(74) *Attorney, Agent, or Firm*—Aaron R. Ettelman; Steven J. Trzaska

(57) ABSTRACT

A method of characterizing an agricultural product at a location, and analysis system, comprising a sensor 2 for generating data, a central processor 4 for receiving the generated data and manipulating the data to calculate a value of at least one property of the product, and displaying the value in the vicinity of the sensor 2. Information is transmitted between sensor 2, central processor 4 and display 6 using a telecommunication link 8.

22 Claims, 1 Drawing Sheet

U.S. PATENT DOCUMENTS

| | | |
|---|---|---|
| 5,616,851 A | 4/1997 | McMahon et al. |
| 5,621,669 A | 4/1997 | Bjornsson |
| 5,644,232 A | 7/1997 | Smith |
| 5,646,078 A | 7/1997 | Mobri et al. |
| 5,689,418 A * | 11/1997 | Monson ................ 382/100 |
| 5,708,593 A | 1/1998 | Saby et al. |
| 5,716,272 A | 2/1998 | Nelson |
| 5,717,209 A | 2/1998 | Bigman et al. |
| 5,751,421 A | 5/1998 | Wright et al. |
| 5,754,289 A | 5/1998 | Ozaki et al. |
| 5,760,399 A | 6/1998 | Trygstad |
| 5,764,819 A | 6/1998 | Orr et al. |
| 5,771,096 A | 6/1998 | Andersen |
| 5,798,526 A | 8/1998 | Shenk et al. |
| 5,850,354 A | 12/1998 | Bramley et al. |
| 5,857,462 A | 1/1999 | Thomas et al. |
| 5,859,435 A | 1/1999 | Satake et al. |
| 5,864,984 A | 2/1999 | McNertney |
| 5,901,237 A | 5/1999 | Conrad |
| 5,917,927 A | 6/1999 | Satake et al. |
| 5,933,792 A | 8/1999 | Andersen et al. |
| 5,936,727 A | 8/1999 | Trygstad |
| 5,952,660 A | 9/1999 | Kip et al. |
| 5,955,737 A | 9/1999 | Hallidy et al. |
| 5,973,324 A | 10/1999 | Saby |
| 5,991,025 A * | 11/1999 | Wright et al. .......... 356/328 |
| 6,002,479 A | 12/1999 | Barwicz et al. |
| 6,014,212 A | 1/2000 | Hammond et al. |
| 6,014,451 A | 1/2000 | Berry et al. |
| 6,031,233 A | 2/2000 | Levin et al. |
| 6,031,608 A | 2/2000 | VonBargen et al. |
| 6,055,487 A | 4/2000 | Margery et al. |
| 6,064,943 A * | 5/2000 | Clark et al. ............... 702/2 |
| 6,069,694 A | 5/2000 | VonBargen |
| 6,096,553 A | 8/2000 | Heald et al. |
| 6,137,108 A | 10/2000 | DeThomas et al. |
| 6,157,041 A | 12/2000 | Thomas et al. |
| 2001/0023410 A1 * | 9/2001 | Hayes et al. ............. 705/26 |

\* cited by examiner

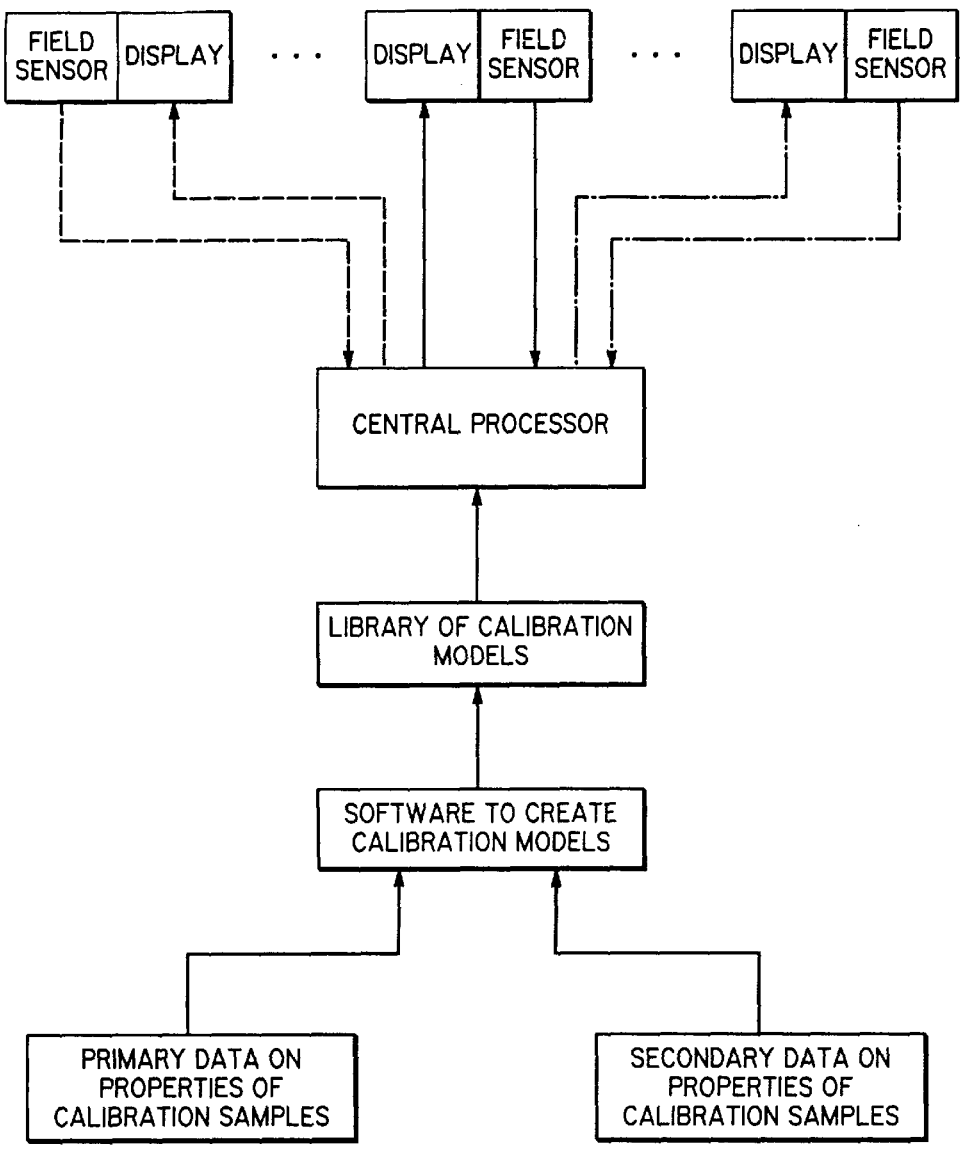

ON-SITE AGRICULTURAL PRODUCT ANALYSIS SYSTEM AND METHOD OF ANALYZING

CROSS-REFERENCE TO RELATED APPLICATIONS

Priority claim to U.S. Provisional Patent Application Serial No. 60/188,500 filed Mar. 10, 2000, the text of which is incorporated herein by reference in its entirety.

STATEMENT REGARDING FEDERALLY SPONSORED RESEARCH OR DEVELOPMENT

Not applicable.

FIELD OF THE INVENTION

The present invention is generally directed to a process for analyzing agricultural products at one or more locations. More particularly, the invention relates to a process for analyzing the traits of various agricultural products including a plant seed, the resulting crop, food items made from the crop, and the like, at various locations where the agricultural crops can be evaluated. The invention also relates to the system for acquiring data at remote site locations, transmitting the data to the central processor for data analysis, and receiving and displaying processed information at those locations.

BACKGROUND OF THE INVENTION

There are numerous instances where one or more properties of an agricultural product are preferably analyzed at one or more locations where the product is found. Agricultural products may be analyzed for the presence and concentration of certain components during the crop growing stage, at harvesting, during transportation or after the product has been stored, as at a grain silo.

It is known to analyze certain components of a particular agricultural product at the location where the material is either grown, harvested, transported, or stored. It may be convenient or necessary for on-site analyzers to be able to be easily transported from one location to another. A portable sensor unit or spectrometer is one that is sufficiently compact and robust to permit it to be transported to alternate testing locations as needed. These units are able to be removed from service and returned to service quickly for transportation to and use at a desired site for analysis. The analytical instruments for such analysis must be rugged and capable of making repetitive analyses with little or no variation over the course of use of the unit.

Because the analysis of a particular agricultural product may need to be determined at locations over a wide geographic area within a narrow time frame, it is impractical to conduct the analyses using only one instrument. Generally it is necessary to test these products at multiple sites with multiple analyzers. The physical condition of the material samples being analyzed, for example the sample temperature, may be different at the various sites, so accommodations must be made in considering the results generated from the material samples.

As discussed herein, a primary measurement involves the use of an instrument or device to determine a characteristic or property of unknown magnitude by comparing the characteristic or property to a reference standard. The instrument used in generating the primary measurement is calibrated to display an output which can be used directly in defining the characteristic or property of interest.

In contrast, a secondary measurement is one produced by an analyzer not capable of measuring the desired property directly. Measurement data are generated, but that data must in turn be correlated into primary data before meaningful information about a characteristic or property of the material can be abstracted. Secondary measurements can be generated using spectroscopic equipment, such as by the use of, for example, the near-infrared and mid-infrared portions of the electromagnetic spectrum.

It is known to use near-infrared spectrometry and mid-infrared spectrometry in commercial processes to monitor the status of chemical reactions. This monitoring capability can involve the generation of secondary measurements with the application of statistical analysis to interpret and quantify the secondary measurement. For example, in the manufacture of carboxylic acids and derivatives from fats and oils, it is known to use near-infrared spectrometers loaded with the appropriate chemometric software to measure a number of properties of the carboxylic acids and their derivatives. This monitoring can be done during the manufacturing process on intermediate product, as well as on the finished product. The spectrometer can be operated in a stand-alone mode with the operator bringing samples to the spectrometer for at-line analysis. Alternatively, the spectrometer can be connected in line to enable monitoring of the process stream as the manufacturing operation proceeds. Thus, two commercially available near-infrared spectrometers such as the Bomem MB-160 FT-NIR spectrometer loaded with HOVAL software (Version 1.6, 1992) and AIRS software (Version 1.54, 1999) from Bomem Inc., Canada, and the Bruker Vector 22/N loaded with the Opus-NT Quant-2 software (Version 2.6, 2000) from Bruker Optik GmbH, Germany have been used to analyze intermediate and finished carboxylic acid products for acid value, iodine value, titer, stearic/palmitic acid ratio in commercial stearic acid, and for the presence of carboxylic acid methyl ester contaminants in a specific carboxylic acid. The calibration models for evaluating the above properties were derived from the Grams-PLS plus (Version 3.01 B, 1994, Galactic Industries Corporation) and Bruker Opus Quant-2. In determining the chemical properties of incoming raw materials such as tallow, coconut oil and palm kernel oil for the production of carboxylic acids, near-infrared spectrometry with appropriate chemometric techniques such as partial least squares (PLS) method has been used to evaluate the free carboxylic acid content of the starting materials, as well as iodine value and moisture content. The near-infrared monitoring can also be used to monitor the progress of the transesterification process utilizing fatty triglycerides and methanol as reactants. A near-infrared spectrometer connected to transesterification process equipment can also monitor free glycerine content, bound/combined glycerine content and methyl ester concentration. Alternatively samples can be taken during the progress of the reaction to a stand-alone near-infrared spectrometer loaded with appropriate calibration models for off-line analysis. In connection with the monitoring of the progress of a reaction, the near-infrared spectrometer can utilize a fiber optic probe connected to the spectrometer by fiber optic cable.

There is presently a high interest in the analysis of agricultural products. Genetically modified materials are of particular interest. The grain and food distribution segments in agriculture have expressed significant need for analytical technology to meet market requirements to identify and quantitate genetically modified crops, especially corn, in world markets. This need has developed rapidly. U.S. farmers have increasingly accepted crops derived from genetic engineering after the success they have experienced in the 1996 growing season. The U.S. Department of Agriculture estimated that approximately 25% of U.S. corn and 54% of U.S. soybeans produced in 2000 were grown from genetically engineered seed with input traits to provide resistance to herbicides, insecticides, or both. The composition of such input trait crops is generally macroscopically indistinguishable from similar crops without the corresponding input traits.

In contrast, the foods of the future which will incorporate improvements of direct benefit to the consumer likely will be based at least in part on crops having enhanced output traits. The composition of these enhanced crops is different from the corresponding conventional crops. Examples include high oil corn, high sucrose soybeans, and low linolenic canola. Genetically-enhanced crops can be produced either by genetic engineering, as enabled by recent advances in biotechnology, or by specially designed traditional breeding programs. Even traditional crop improvement practices can result in plants with changed genetics and enhanced properties.

The growth and the need for analytical technology for agricultural products has been the promulgation of labeling relations adopted in many regions of the world including the two largest agricultural commodity trading communities, the European Union and Japan. These labeling requirements have required or are expected to require food processors to label finished food products as to the genetically modified content of the ingredients used to produce these products. The initiation of labeling and the growing number of food processors electing to use raw materials which have not been genetically modified are driving the need for identity preservation.

Labeling specifications are nearing completion in both Europe and Japan. Identifying the genetic composition of grain in commercial crops and maintaining that identity throughout the agricultural complex to support labeling has become a high priority for seed companies, commercial growers, distribution and process companies, as well as food processors and is expected to increase as labeling is further implemented in the future.

A problem associated with the use of conventional testing procedures to determine whether seeds and/or crops have been genetically enhanced or to quantitatively determine the percentage of genetically modified substances in a material is that they involve an analysis of the genetic code, i.e., DNA of the seed crop, or of proteins produced by specific genes of the DNA. DNA testing such as this may be a time consuming or an expensive procedure, or may yield only semi-quantitative results. Furthermore, these types of analyses do not determine the effectiveness of the genetic code in modifying the chemical composition of an existing output trait or in creating one or more new chemical components in a new output trait. Consequently there is a need to provide an economical and efficient way to analyze seeds and crops at various locations along the supply chain, to identify and quantify the chemical composition and potentially other measurable properties of one or more output traits in genetically enhanced as well as conventional crops.

BRIEF SUMMARY OF THE INVENTION

The present invention is directed to a process for identifying and quantifying one or more traits of an agricultural product, the process involving:

(a) providing a material to be analyzed;

(b) providing at least one transportable sensor capable of acquiring data for analysis of the material;

(c) providing a centralized database of chemometric models of trait data corresponding to the material;

(d) analyzing the material using the transportable sensor in order to obtain material trait data;

(e) providing a computer capable of storing the database of chemometric models of trait data, and computing the material characteristics using the chemometric models;

(f) providing a telecommunication link between sensor and computer; and (g) displaying at least one result from the computed material characteristics in the vicinity of the sensor.

The sensors acquire data for spectroscopic analyses. Preferably, the transportable sensors are capable of performing secondary measurements for analysis of the material at a number of remote locations. The database of chemometric models is constructed from primary measurement data on one or more properties of interest of the agricultural product.

The invention is also directed to an analysis system for analyzing the agricultural products.

At a basic level, the system comprises one or more sensors, a central processor, and a telecommunications link. The sensors are used primarily for data acquisition, and the central processor for data analysis. The sensors are physically separated from the central processor, and are often remote from each other, though two or more sensors may be at a single location. The central processor stores a database of chemometric models, receives spectroscopic data acquired by the sensors about the particular material, computes characteristics or properties of the material using the chemometric models, and sends the results back to the sensors. The sensors and central processor communicate with each other via transmission of information over the telecommunications link. Presently, it is preferred that the information be transmitted in a digital form. The telecommunications link may be a hard wire telephone system, a tower or satellite based wireless system, or combinations sufficient to transmit a signal between any location and a central processor.

In the analysis of agricultural products, particularly for grain transactions, it is important to be able to determine the properties or characteristics of the crop with a minimum of time delay. Traditionally, the laboratory analysis of a particular agricultural product may result in two to four days delay from the time of sample acquisition to the final determination of properties or characteristics, primarily due to the time required to ship samples to a laboratory capable of performing the required analysis. It is also important that the properties of the agricultural product in one location be able to be compared with the properties of the same agricultural product at a separate location, often times separated by a substantial geographic distance. In the practice of the invention, it is therefore an advantage to be able to undertake analyses at multiple locations, whether or not geographically distant, and process the data acquired on a particular sample through a single central processor. Even where only a single sensor is connected to the central processor, that single sensor is able to acquire data and forward it to the central processor for manipulation, which results ultimately in a secondary data measurement having the sophistication of the chemometric model loaded into the central processor without the need of actually transporting the central processor into the field.

In the event that connection between the sensor and central processor is interrupted, a portable computer such as a properly configured laptop unit loaded with the most recent library of calibration models may be used to interface directly with the sensor. The laptop would thus function as a mobile central processor. This use would be considered as an alternative to a central processor; the preferred device would be the central processor.

It is therefore an object of the invention to provide a method of analysis for agricultural products which permits a measurement of one or more properties of materials located in remote locations by utilization of a single calibration model for each trait.

It is a further object of the invention to provide an analysis system which incorporates a display unit in combination with the sensor to provide analysis information generated by a central processor for a particular sample being measured, at the location where the measurement is taken.

It is a further object of the invention to provide an analysis system which provides for multiple remote sensors and a central processor which can generate analysis data on multiple agricultural products remote from each other but which are each analyzed using the same calibration model for the particular property being measured.

It is a further object of the invention to provide a method of analysis which permits the measurement of one or more properties of agricultural products located in remote locations utilizing a single calibration model for each trait.

These and other objects and advantages of the invention are provided in the detailed description of the invention and in the drawing.

BRIEF DESCRIPTION OF THE DRAWING

The FIGURE is a block diagram depicting the relation between the central processor, the sensor units, and the library of calibration models.

DETAILED DESCRIPTION OF THE INVENTION

Other than in the operating examples, or where otherwise indicated, all numbers expressing quantities of ingredients or reaction conditions are to be understood as being modified in all instances by the term "about".

The invention is directed in its broader aspects to a method of characterizing an agricultural product at a location comprising analyzing an agricultural product with at least one sensor to generate and acquire data, transmitting the acquired data by a telecommunication link to a central processor, manipulating the acquired data by the central processor to calculate the value of at least one property characterizing the agricultural product where the central processor contains a library of calibration models, and transmitting the data measurement by the telecommunication link to a display in the vicinity of the sensor.

The invention is also directed to an analysis system comprising at least one sensor for acquiring data, a central processor storing calibration models for traits which are of interest, a telecommunications link connecting the sensor and the central processor, and a display in the vicinity of the sensor to receive the primary data measurement of interest calculated by the central processor. In one embodiment, the display may be a display panel affixed to the sensor.

In connection with the analysis of crop samples, typically there are two groups of traits which are considered in this evaluation. These traits are known as input traits and output traits. The input traits are those which are considered as inputs to the process of producing the crop. Thus, for example, the characteristics of herbicide resistance and insect resistance would be considered as input traits. Other agronomic inputs independent of the characteristics of the crop seed include fertilizer, water, sunlight, soil conditions and the like.

In contrast, output traits of a crop generally refer to composition characteristics. For example, high oil content is an output trait for corn, as is high sucrose for soybeans, and low linolenic triglyceride for canola seed. Crops which are potential subjects for near-infrared analysis in the field are any which might either involve genetic enhancement through genetic engineering or through specifically designed traditional breeding programs, or traditional crops whose characteristics may need to be analyzed for identifying or assessing the value of the crop. It can be appreciated that the costs involved in generating analyses of crop samples would support testing of genetically enhanced crops because of the potential for increased value of that product. Nonetheless, any crop sample may be the subject for analysis using the techniques.

A sensor 2 as used herein is a device comprising one or more detectors appropriately chosen to acquire data about one or more properties of interest of a material. The sensor 2 optionally includes an excitation source, a sample handling device to present the sample to the detector, and associated electronics to convert the detector output into a particular data format. Conversion into a particular data format can include the capacity to perform data pre-processing at the sensor 2. Presently, it is preferred to convert the detector output into a digitized format. In the preferred embodiment of the present invention, the detector information is optionally pre-processed and converted into a digital format to facilitate rapid communication and subsequent data processing. Pre-processing steps may be used to simplify the raw data and reduce experimental noise by mathematical operations such as, but not limited to, filtering the data to reduce its size to one or more smaller regions of interest and eliminate data from non-interesting regions, and applying one or more mathematical transformations such as weighting, Fourier transform, multiplicative scatter correction, baseline corrections, and derivatives. While another embodiment could utilize the transmission of unprocessed spectral data the preferred embodiment is advantageous in that digitization occurs prior to transmission.

The central processor 4 as used herein is a computer system that is used to store and manipulate a centralized library of calibration models, to execute computational software to perform the chemometric analysis, and to communicate results to the corresponding sensor unit for display. The term "chemometrics" is used to identify the nature of the analysis because the term embraces multivariate analysis, and it relates measured values to parameters in a physicochemical model. The interpretation of the computed results, for example, component concentrations, is based on chemistry. The processor 4 is not necessarily a single entity, however, since it may reside on multiple computer servers, where some duplication may be provided for redundancy and other duplication may be provided to mirror the servers in multiple geographic locations. In practice, the processor behaves as if it were a single entity at a central location. The model library is actually maintained on a single, primary server and this is duplicated as need to provide for redundancy and mirroring. Henceforth, the group of redundant and mirrored processors will simply be called the central processor.

An unusual master-slave relationship is established between the sensors 2 and the central processor 4. Since data acquisition is initiated at the sensors 2, the central processor 4 becomes a slave to the numerous sensors 2 in the field. The sensors 2 are not self-contained analyzers, but are dependent on the central processor for data analysis. Thus, the sensors are dumb masters and the central processor 4 is a smart slave in a many-to-one relationship.

The term "remote" as used herein is intended to only identify the existence of a physical separation between the sensor and the central processor. A remote sensor is not intended to suggest that the sensor location is isolated geographically or technologically from the central processor.

The library of calibration models stored on the central processor 4 can be modified as desired to provide calibration updates, add calibration models to expand the capabilities for analyzing new traits or crops, or to delete calibration models that are no longer needed. All modifications to the database of the central processor 4 can be done without making any changes to the hardware or software of individual sensors 2. The drawing shows how the library is created from primary and secondary data and how this library is used to compute values of traits from the on-site measurement data.

The user interface of the display located in the vicinity of the sensor 2 can provide a selectable menu of trait measurements that are available at the central processor 4. Prior to each measurement, for example, the central processor 4 can transmit the current list of available trait measurements to the sensor unit 2. In this way, the user will always access from the updated selectable menu displayed at the sensor 2 the most current list of available trait measurements as well as the most current revision to all calibration models without needing to manually install software updates to replace, change, add, or delete calibration models or some parameters of the calibration models as would need to be done if the models were stored in a computing device connected to each sensor 2.

In the practice of the method of analysis and use of the analysis system, at least one sensor 2 is transported to a location where the analysis of an agricultural crop is to be conducted. As it can be appreciated that agricultural products are produced in geographically distant locations, the sensor 2 should be able to be transported to any site preferably by the user of the sensor 2. The sensor 2 should additionally be capable of withstanding transport without causing damage to the internal components, and should be able to resist any climatic affects which may be encountered during the analysis. One product which can be used as a sensor 2 is the MATRIX-F Fourier-Transform near-infrared spectrometer manufactured by Bruker Optik GmbH. This particular product is available either with dustproof or waterproof housings.

The central processor 4 may be implemented using any electronic device or combination of devices (e.g., one or more servers) capable of hosting models, applying the models to sensor data and generating and outputting the results to the sensors 2.

The information returned from the central processor 4 is posted on a display 6. This display 6 is located in the vicinity of the sensor 2, and preferably is attached to the sensor 2.

The telecommunications link 8 broadly is any means whereby a connection can be effected between the sensor and central processor. Preferably, the connection is via the Internet, but can also include hard wire connection, wireless connection, tower based or satellite based wireless connection or combinations.

The sensor 2, such as the above mentioned Bruker MATRIX-F unit, and the central processor must be enabled to communicate with each other. This can be effected by the use of appropriate software and hardware user interface connections.

Preferably, the analysis system is capable of receiving requests for data manipulation at the central processor 4 from multiple sensors 2 at any time. Thus, real time processing and scalability is required. For example, in one embodiment, upon acquisition of data at the sensor 2, a test operator may forward the data in some format, preferably digital, to the central processor 4. The processor 4 will be equipped with a first-in first-out queuing capability as well as an event triggering mechanism. Data forwarded from the sensors 2 may be stacked in a queue, the central processor 4 then taking the requests for analysis off the stack in order.

Because the number of sensors 2 requesting data manipulation at any one time will usually be unknown, the central processor 4 must typically be able to handle a large number of requests at one time.

In the operation of the analysis system, the sensor 2 may incorporate a running application which posts information about the sensor, such as location, user, and the like, along with sample data to a web page. The web page may be configured to instantiate the interface between the sensor 2 and the central processor 4, move the acquired data into a message repository, and wait for the status of the message to change. These steps may all occur on a web server. The software running on the central processor 4 may wait for a new message and instantiates one or more controller programs, which subsequently launch one or more processor 4 programs to begin reading the acquired data lodged in the message repository. The processor 4 programs may utilize the appropriate calibration models to calculate the primary data measurement and update the message in the queue to include the results of the calculations. Finally, the web page may be configured to see that the status of the message has changed in the message repository, and forward the results back to the sensor 2, typically to a display panel 8 or other display device in the vicinity of the sensor 2. The message may then be removed from the message queue.

By relying on a set of controller and processor 4 programs to handle requests, such components can be selected from a library of reusable components to provide customized request handling functionality with substantially reduced custom program code. Moreover, the ability to track and handle messages placed on a queue in the manner disclosed herein provides a robust and scalable communications network for handling essentially real-time communications between the sensors 2 and the central processor 4, typically without concern for any disparities in response times for the sensors 2 and/or central processor 4.

It should be appreciated, however, that any form of communication network and/or protocol that permits requests from multiple sensors 2 to be routed to and processed by a central processor 4 may be used in the alternative.

In operation, the system can place one or more sensors 2 in crop growing areas in Canada to measure, for example, properties of canola seed. The sensors 2, such as the Bruker MATRIX-F spectrometer, can be operated by a vendor of the analysis service, by a farmer, silo operator, or other person or company. Canola seed is fed into a sample presentation device non-destructively so it passes across the beam emitted from a near-infrared fiber optic probe at the sensors 2. Data generated is then transmitted to a central processor 4 loaded with appropriate chemometric software, such as HOVAL software (Version 1.6, 1992), AIRS software (Version 1.54, 1999) or Bruker Opus-NT Quant-2 software (Version 2.6, 2000), via an Internet connection. After manipulating the data from the sensors 2 in the order received, the central processor 4 returns results calculated from the appropriate chemometric model relevant to the property of interest to the display 6 mounted on the sensors 2.

Alternatively, in some situations, it may be desirable to increase the sample homogeneity by grinding the sample prior to data acquisition. On other occasions, it may be desirable to crush the sample, for example to express oil from oilseeds, or to perform more complex sample preparation, for example to extract components from the sample or to add one or more chemical reagents to the sample, to chemically convert the sample or a portion of the sample into a form more suitable for some types of analysis.

Having described this invention and its operating parameters, variations may be achieved without departing from the spirit and scope hereof.

What is claimed is:

1. A method of characterizing an agricultural product at a location comprising:

analyzing an agricultural product with at least one sensor to generate and acquire data;

transmitting the acquired data by a telecommunication link to a central processor; containing a library of calibration models manipulating the acquired data by the central processor to calculate the value of at least one property characterizing the agricultural product, and transmitting the data measurement by the telecommunication link to display in the vicinity of the sensor.

2. The method of claim 1 comprising multiple sensors.

3. The method of claim 1 wherein each calibration model in the central processor is modifiable.

4. The method of claim 1 wherein the library of calibration models in the central processor is modifiable.

5. The method of claim 1 further comprising characterizing at least one output trait of the agricultural product.

6. The method of claim 1 wherein the agricultural product is analyzed with radiation in the near-infrared range.

7. The method of claim 6 wherein the agricultural product is analyzed with a Fourier transform near-infrared sensor.

8. The method of claim 1 wherein the telecommunication link is a Internet connection.

9. The method of claim 1 wherein the telecommunication link is a telephonic connection.

10. The method of claim 1 wherein the telecommunication link is a wireless connection.

11. The method of claim 2 further comprising analyzing multiple agricultural products with multiple sensors.

12. The method of claim 11 wherein the multiple agricultural products have substantially the same composition.

13. The method of claim 11 wherein the multiple agricultural products have different compositions.

14. An analysis system for analyzing one or more properties of an agricultural product comprising:

at least one sensor for acquiring data from an agricultural product;

a central processor containing a library of calibration models connected to the sensor over a telecommunication link for manipulating acquired data to generate at least one data measurement; corresponding to at least one property characterizing the agricultural product; and a display in the vicinity of the sensor to display the data measurement from the central processor.

15. The analysis system of claim 14 having more than one sensor.

16. The analysis system of claim 14 wherein the central processor contains a library of calibration models.

17. The analysis system of claim 16 wherein the calibration models are modifiable.

18. The analysis system of claim 16 wherein the library of calibration models is modifiable.

19. The analysis system of claim 14 wherein the telecommunication link is an Internet connection.

20. The analysis system of claim 14 wherein the telecommunication link is a telephonic connection.

21. The analysis system of claim 14 wherein the telecommunication link is a wireless connection.

22. The analysis system of claim 14 wherein the display is mounted to the sensor.

* * * * *